(12) United States Patent
Carrasco Zanini et al.

(10) Patent No.: US 10,343,276 B2
(45) Date of Patent: Jul. 9, 2019

(54) COMPACT MAGNETIC CRAWLER VEHICLE WITH ANTI-ROCKING SUPPORTS

(71) Applicant: Saudi Arabian Oil Company, Dhahran (SA)

(72) Inventors: Pablo Carrasco Zanini, Thuwal (SA); Fadl Abdellatif, Thuwal (SA); Abdullah Arab, Thuwal (SA); Brian Parrott, Thuwal (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 107 days.

(21) Appl. No.: 15/647,332

(22) Filed: Jul. 12, 2017

(65) Prior Publication Data

US 2019/0015971 A1 Jan. 17, 2019

(51) Int. Cl.
*B25J 5/00* (2006.01)
*B60B 19/00* (2006.01)
(Continued)

(52) U.S. Cl.
CPC ............ *B25J 5/007* (2013.01); *B60B 19/006* (2013.01); *B62D 53/028* (2013.01);
(Continued)

(58) Field of Classification Search
CPC ........................... B60B 19/006; B62D 55/265
See application file for complete search history.

(56) References Cited

U.S. PATENT DOCUMENTS 5,610,488 A 3/1997 Miyazawa
5,809,099 A 9/1998 Kim et al.
(Continued)

FOREIGN PATENT DOCUMENTS

CN 2108007 U 6/1992
CN 104787144 A 7/2015
(Continued)

OTHER PUBLICATIONS

No Author. "ThetaScan: A Manual Ultrasonic C-scan Imaging System." SilverWing. No date. 1 page.
(Continued)

*Primary Examiner* — Kevin Hurley
(74) *Attorney, Agent, or Firm* — Leason Ellis LLP

(57) ABSTRACT

A robotic vehicle for traversing surfaces is provided. The vehicle is comprised of a chassis supporting a magnetic drive wheel for driving and steering the vehicle and a stabilization mechanism. The magnetic wheel comprises two flux concentrator yokes and an axially magnetized hub extending therebetween. The hub includes a central housing configured to house a sensor probe and enhance the magnetic pull force of the wheel by providing a continuous pathway of high magnetic permeability material for magnetic flux to flow axially through the drive wheel. The stabilization mechanism comprises a front and rear facing support element moveably coupled to the chassis and configured to contact the surface and move symmetrically relative to the chassis thereby maintaining the vehicle and probe normal to the surface and providing stability to the vehicle while traversing surfaces regardless of surface curvature and vehicle orientation.

24 Claims, 10 Drawing Sheets

(51) Int. Cl.
  *B62D 53/02* (2006.01)
  *B62D 57/028* (2006.01)
  *G01N 29/34* (2006.01)
  *B62D 57/024* (2006.01)
(52) U.S. Cl.
  CPC ......... *B62D 57/024* (2013.01); *B62D 57/028* (2013.01); *G01N 29/34* (2013.01)

(56) References Cited

U.S. PATENT DOCUMENTS

| | | |
|---|---|---|
| 8,604,900 B2 | 12/2013 | Kocijan |
| 2014/0345957 A1 | 11/2014 | Bernstein et al. |
| 2017/0348850 A1* | 12/2017 | Nguyen ................ B60B 19/006 |
| 2017/0355225 A1* | 12/2017 | Lee ......................... B63B 59/08 |
| 2018/0232874 A1* | 8/2018 | Ostervold ............. G06T 7/0004 |

FOREIGN PATENT DOCUMENTS

| | | |
|---|---|---|
| GB | 23491 A | 9/1903 |
| SI | 9700050 A | 10/1998 |
| WO | 2011017668 A2 | 2/2011 |

OTHER PUBLICATIONS

International Search Report and Written Opinion for corresponding International Patent Application No. PCT/US2018/041044 dated Oct. 17, 2018. 22 pages.

* cited by examiner

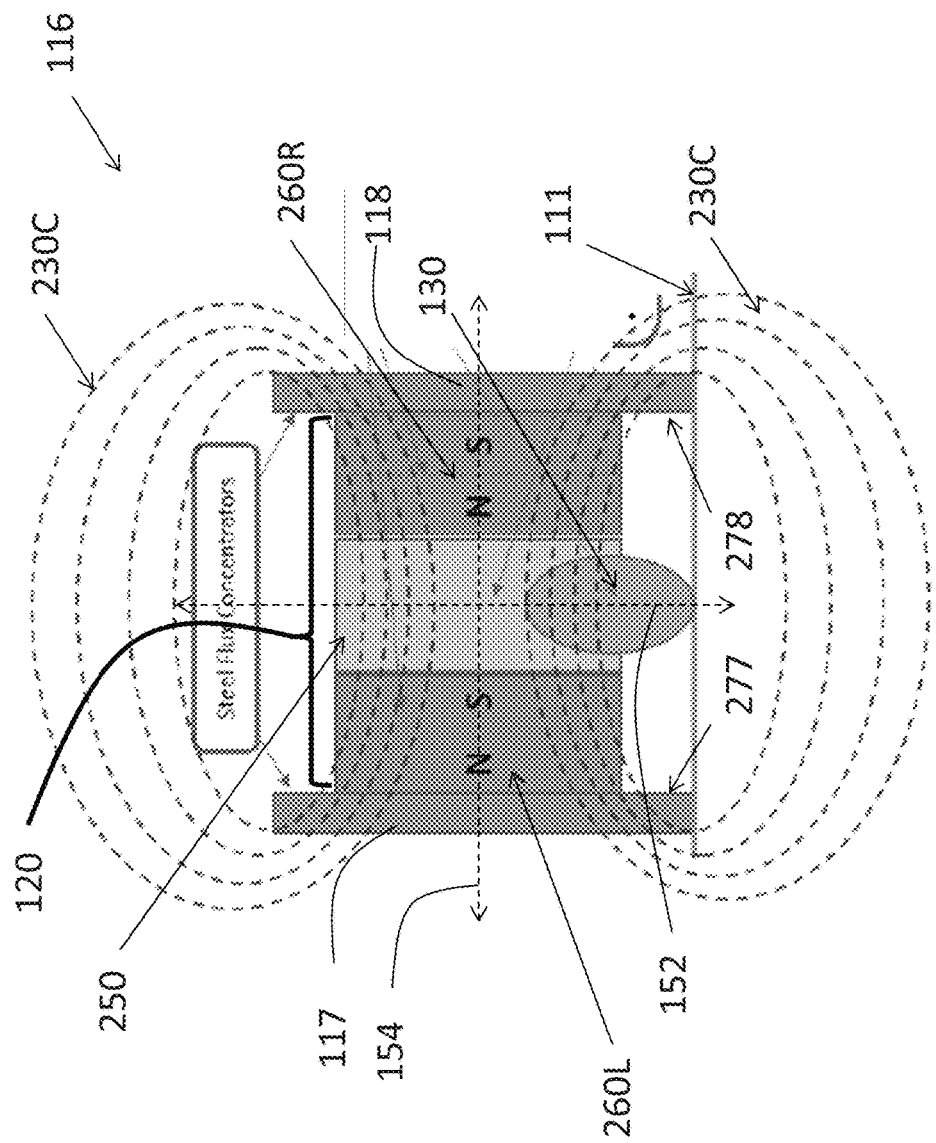

COMPACT MAGNETIC CRAWLER VEHICLE WITH ANTI-ROCKING SUPPORTS

FIELD OF THE INVENTION

The present invention relates to robotic vehicles and, in particular, robotic inspection vehicles having a magnetic drive wheel.

BACKGROUND OF THE INVENTION

Routine inspection of equipment is critical in most industries in order to ensure safety and optimize performance. For example, in the petroleum industry and related fields, liquids and gases and mixtures thereof are transported via pipelines and these materials are also stored in large tanks.

It is known in this industry that in order to maintain the integrity of pipelines, storage tanks and the like, a sensor device can be employed to inspect such surfaces. In particular, an inspection vehicle can be used to travel across a surface of the target object (e.g., a pipe or tank) and record information about the quality of the pipe wall. A majority of these inspection vehicles use ultrasonic or magnetic sensors to carry out the inspection. Based on the recorded information, any cracks or other deficiencies in the surface being inspected (e.g., pipe wall) can be detected and noted to allow for subsequent remedial action to be taken.

In the past, there have been different inspection vehicle designs that are used to inspect various structures, such as factory equipment, ships, underwater platforms, pipelines and storage tanks. If a suitable inspection vehicle is not available to inspect the structure, an alternative is to build scaffolding that will allow people access to inspect these structures, but at great cost and danger to the physical safety of the inspectors. Past inspection vehicles have lacked the control, maneuverability and compact packaging (i.e., size) necessary to inspect such surfaces effectively.

In addition, while there are a number of different sensors that can be used in such inspection vehicles, one preferred type of ultrasonic sensor is a dry coupled probe (DCP) that is configured to perform ultrasonic inspection of the surface to measure wall thickness and detect corrosion. Dry coupled probes are typically built in the form of a wheel in which a shaft (axle) is meant to be held fixed since the shaft has the transducer component rigidly embedded in it while an outer tire rotates around the shaft. The shaft of the probe thus must be held and positioned such that the transducer always points at the surface, meaning that the wheel is not titled in its roll and pitch directions.

Thus, one of the challenges in using a DCP is that the probe needs to always be perpendicular (normal) to the surface being inspected and this can be a challenge while the inspection vehicle is mobile and navigating the surface. A further challenge is to maintain the probe in close proximity or in contact with the surface being inspected. This is especially difficult since the inspection vehicle can drive circumferentially, longitudinally and helically on a pipe or tank surface which means that the DCP has to be realigned to ensure that the DCP is normal to the surface being inspected regardless of the location of the inspection vehicle.

The present invention provides a solution for providing vehicular movement in non-gravity-dependent operations, where the impact of gravity on vehicle movement can be minimized while still enabling versatile control. As well, the present invention is capable of maintaining stability and effectively navigating a variety of curved surfaces such as pipes and vessels, as this is one possible use of the invention. The present invention is also directed to a mechanism (device/apparatus) that stabilizes, maintains an appropriate height of the sensor and normalizes the of the sensor (e.g., DCP) relative to the surface being inspected when inspection is being performed and while the inspection vehicle is being steered and/or moved in a variety of different tracks along the surface despite a varying range of degrees of curvature of the surface.

It is with respect to these and other considerations that the disclosure made herein is presented.

SUMMARY OF THE INVENTION

According to an aspect of the present invention, a magnetic robotic crawler vehicle for traversing a surface is disclosed. The vehicle comprises a chassis and a magnetic drive wheel that is mounted to the chassis such that the drive wheel extends in a lateral direction. In addition, the drive wheel comprises two spaced apart flux concentrating yokes that rotate about a rotational axis and an axially magnetized hub extending laterally between the two yokes. The yokes are configured to be driven independently thereby driving and steering the vehicle along the surface. For reference, the vehicle has a longitudinal axis that extends perpendicularly to the rotational axis in a front and back direction and through the midpoint between the two yokes.

In addition, the vehicle further comprises a stabilization mechanism that is coupled to the chassis. In particular, the stabilization mechanism comprises a first "front facing" support element and a second "rear facing" support element configured to contact and move along the surface during normal operation of the vehicle. The first and second support elements are positioned on opposite sides of the drive wheel relative to the rotational axis, and are positioned symmetrically with respect to the longitudinal axis. The stabilization mechanism also includes a support mechanism moveably coupling the first and second support elements to the chassis. The support mechanism is configured to move the first and second support elements relative to the chassis in at least an up and down direction. In particular, the support mechanism is passive in nature and moves the first and second support elements in the up and down direction in response to a curvature of the surface thereby maintaining the first and second support elements in contact with the surface.

According to a further aspect, the vehicle further comprises one or more position sensors attached to one or more of the stabilization mechanism, the chassis and the drive wheel. The one or more position sensors are configured to measure a relative position between the stabilization mechanism and either the drive wheel or the chassis. The vehicle further comprises a processor that, based on a known geometry of the stabilization mechanism and the drive wheel and the relative position measured using the one or more sensors during execution of a prescribed maneuver of the robotic crawler vehicle on the surface, is configured to calculate a) an orientation of the robotic crawler vehicle relative to the surface in view of a known geometry of the surface, and/or b) calculate a curvature of the surface.

According to a further aspect, the vehicle further comprises one or more position sensors attached to one or more of the sensor probe assembly, the chassis and the drive wheel. In particular, the one or more position sensors are configured to measure a relative position between the sensor probe assembly and the drive wheel. In addition, the vehicle further comprises a processor that, based on a known geometry of the sensor probe assembly and the drive wheel and the relative position measured using the one or more sensors during execution of a prescribed maneuver of the robotic crawler vehicle on the surface, is configured to calculate a) an orientation of the robotic crawler vehicle relative to the surface in view of a known geometry of the surface, and/or b) calculate a curvature of the surface.

According to another aspect of the present invention, a magnetic robotic crawler vehicle for traversing a surface is disclosed. The vehicle comprises a chassis and a magnetic drive wheel that is mounted to the chassis such that the drive wheel extends in a lateral direction. More specifically, the drive wheel comprises two spaced apart flux concentrating yokes and an axially magnetized hub extending laterally therebetween. The yokes rotate about a rotational axis and are configured to be driven independently thereby driving and steering the vehicle along the surface. For reference, a longitudinal axis of the vehicle extends perpendicularly to the rotational axis in a front and back direction and through the midpoint between the two yokes.

The axially magnetized hub extending laterally between the two yokes comprises one or more axially magnetized magnets, and a housing. The housing is composed of a ferromagnetic material and includes a left wall, an opposing right wall and a one or more lateral walls extending therebetween along the rotational axis. In addition, the walls of the housing are shaped to define an open chamber therein and the one or more lateral walls are shaped to define at least one opening therethrough. Furthermore, the chamber is provided at the midpoint between the two yokes and the housing has a fixed position relative to the yokes such that the at least one opening faces downward toward the surface during normal operation of the vehicle.

The vehicle further comprises a stabilization mechanism that is coupled to the chassis, the stabilization mechanism comprising a first and a second support element configured to contact and move along the surface during normal operation of the vehicle. In particular, the first and second support elements being positioned on opposite sides of the drive wheel relative to the rotational axis and are positioned symmetrically across the rotational axis of the drive wheel and symmetrically with respect to the longitudinal axis. Moreover, the stabilization mechanism includes a support mechanism that moveably couples the first and second support elements to the chassis. In particular, the support mechanism is configured to move the first and second support element relative to the chassis in at least an up and down direction. Moreover, the support mechanism is passive in nature and moves the first and second support elements in the up and down direction in response to a curvature of the surface thereby maintaining the first and second support elements in contact with the surface.

According to another aspect of the present invention, a magnetic robotic crawler vehicle for traversing a surface is disclosed. The vehicle comprises a chassis and a magnetic drive wheel that is mounted to the chassis such that the drive wheel extends in a lateral direction. More specifically, the drive wheel comprises two spaced apart flux concentrating yokes and an axially magnetized hub extending laterally therebetween. The yokes rotate about a rotational axis and are configured to be driven independently thereby driving and steering the vehicle along the surface. For reference, a longitudinal axis of the vehicle extends perpendicularly to the rotational axis in a front and back direction and through the midpoint between the two yokes.

The axially magnetized hub extending laterally between the two yokes comprises one or more axially magnetized magnets, and a housing. The housing is composed of a ferromagnetic material and includes a left wall, an opposing right wall and a one or more lateral walls extending therebetween along the rotational axis. In addition, the walls of the housing are shaped to define an open chamber therein and the one or more lateral walls are shaped to define at least one opening therethrough. Furthermore, the chamber is provided at the midpoint between the two yokes and the housing has a fixed position relative to the yokes such that the at least one opening faces downward toward the surface during normal operation of the vehicle.

The vehicle further comprises a sensor probe assembly disposed at least partially within the chamber of the housing. In particular, the sensor probe assembly comprises a dry coupled wheel probe and a sensor support. The wheel probe is configured to passively roll generally in a direction of travel of the vehicle along the surface. The sensor support moveably couples the wheel probe to one or more of the housing and the chassis. In addition, the sensor support assembly is configured to passively move the wheel probe relative to the housing in at least the up and down direction in response to the curvature of the surface thereby maintaining the probe in contact with the surface during normal operation of the vehicle.

The vehicle further comprises a stabilization mechanism that is coupled to the chassis, the stabilization mechanism comprising a first and a second support element configured to contact and move along the surface during normal operation of the vehicle. In particular, the first and second support elements being positioned on opposite sides of the drive wheel relative to the rotational axis and are positioned symmetrically across the rotational axis of the drive wheel and symmetrically with respect to the longitudinal axis. Moreover, the stabilization mechanism includes a support mechanism that moveably couples the first and second support elements to the chassis. In particular, the support mechanism is configured to move the first and second support element relative to the chassis in at least an up and down direction. Moreover, the support mechanism is passive in nature and moves the first and second support elements in the up and down direction in response to a curvature of the surface thereby maintaining the first and second support elements in contact with the surface.

These and other aspects, features, and advantages can be appreciated from the accompanying description of certain embodiments of the invention and the accompanying drawing figures and claims.

BRIEF DESCRIPTION OF THE DRAWING FIGURES

FIG. 2C is a rear-view conceptual diagram of the magnetic drive wheel of the magnetic robotic crawler vehicle of FIG. 1A in accordance with one or more disclosed embodiments;

Figure 4:
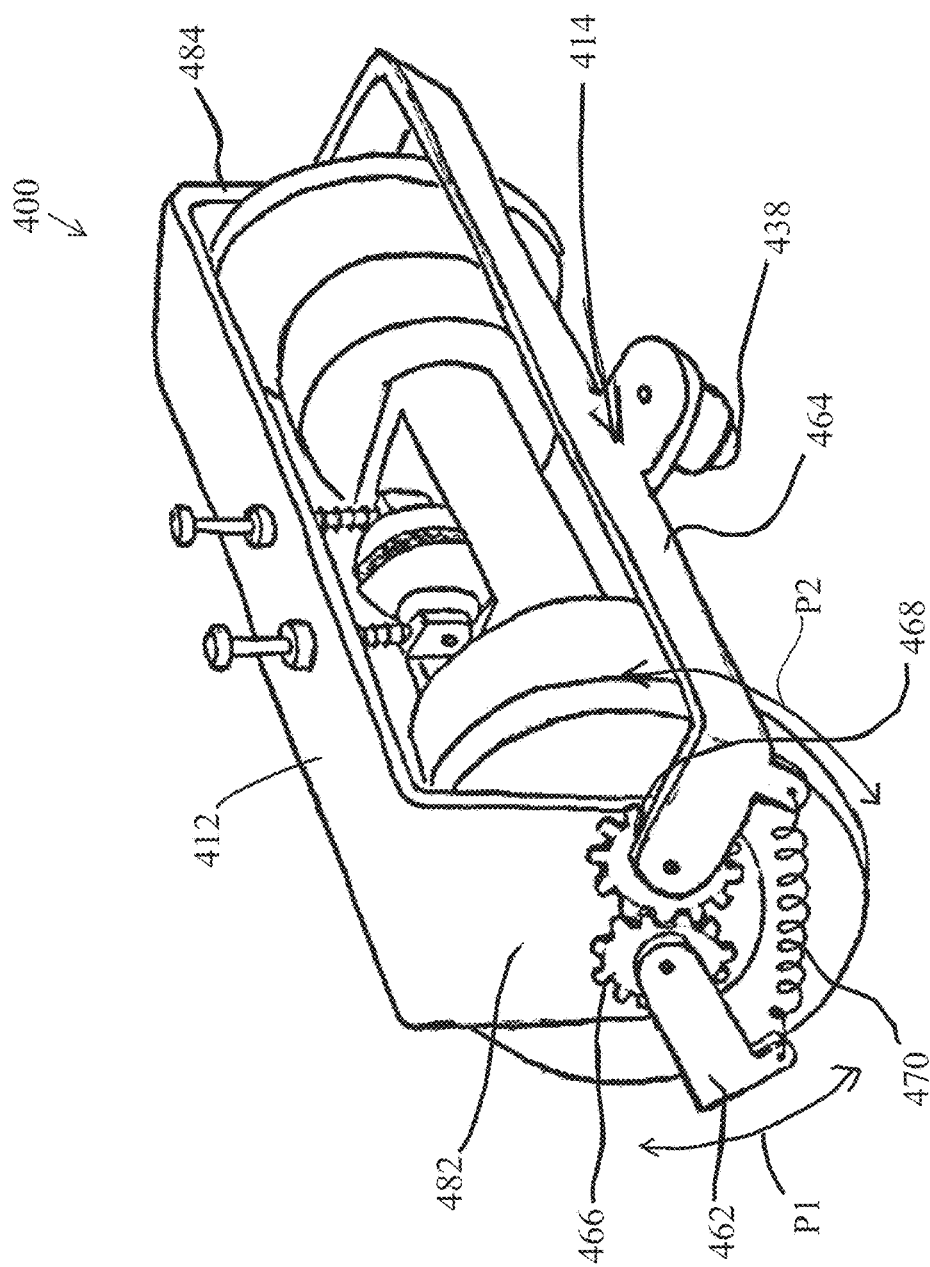
Figure 5:
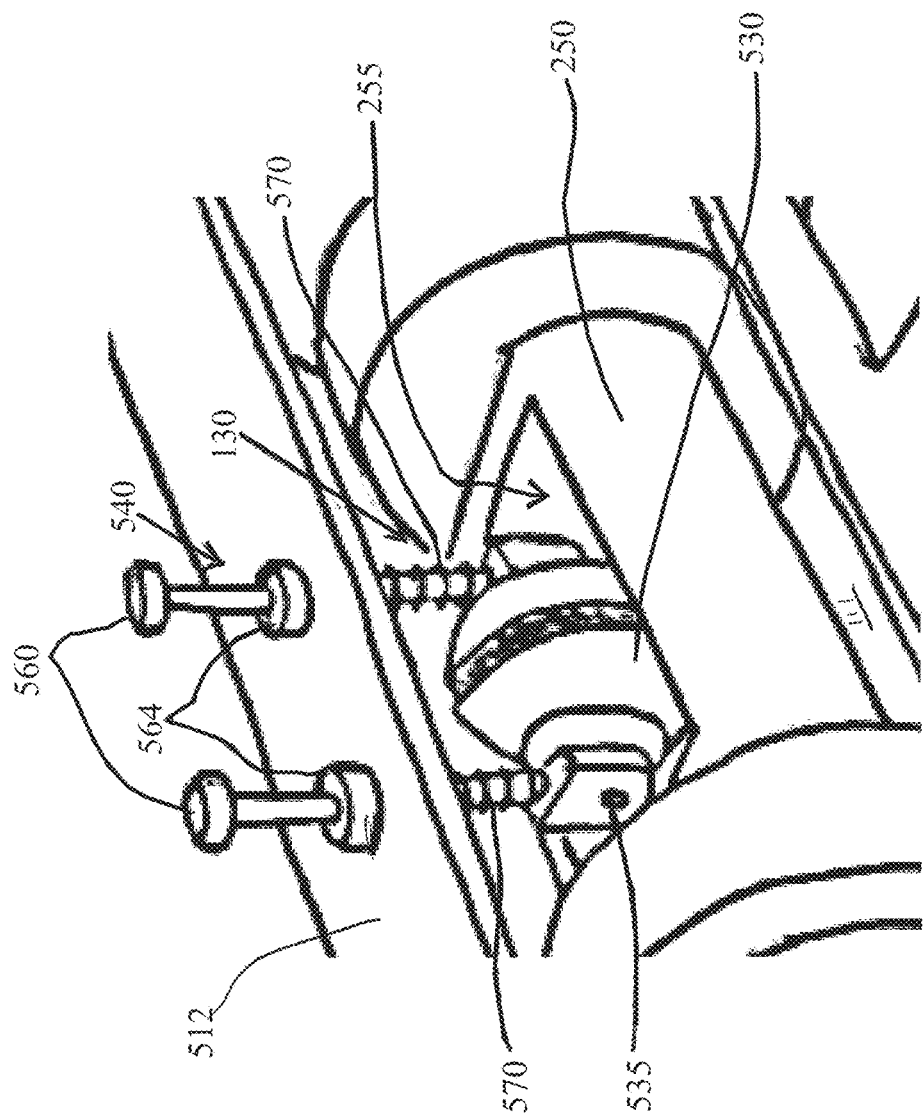
Figure 6:
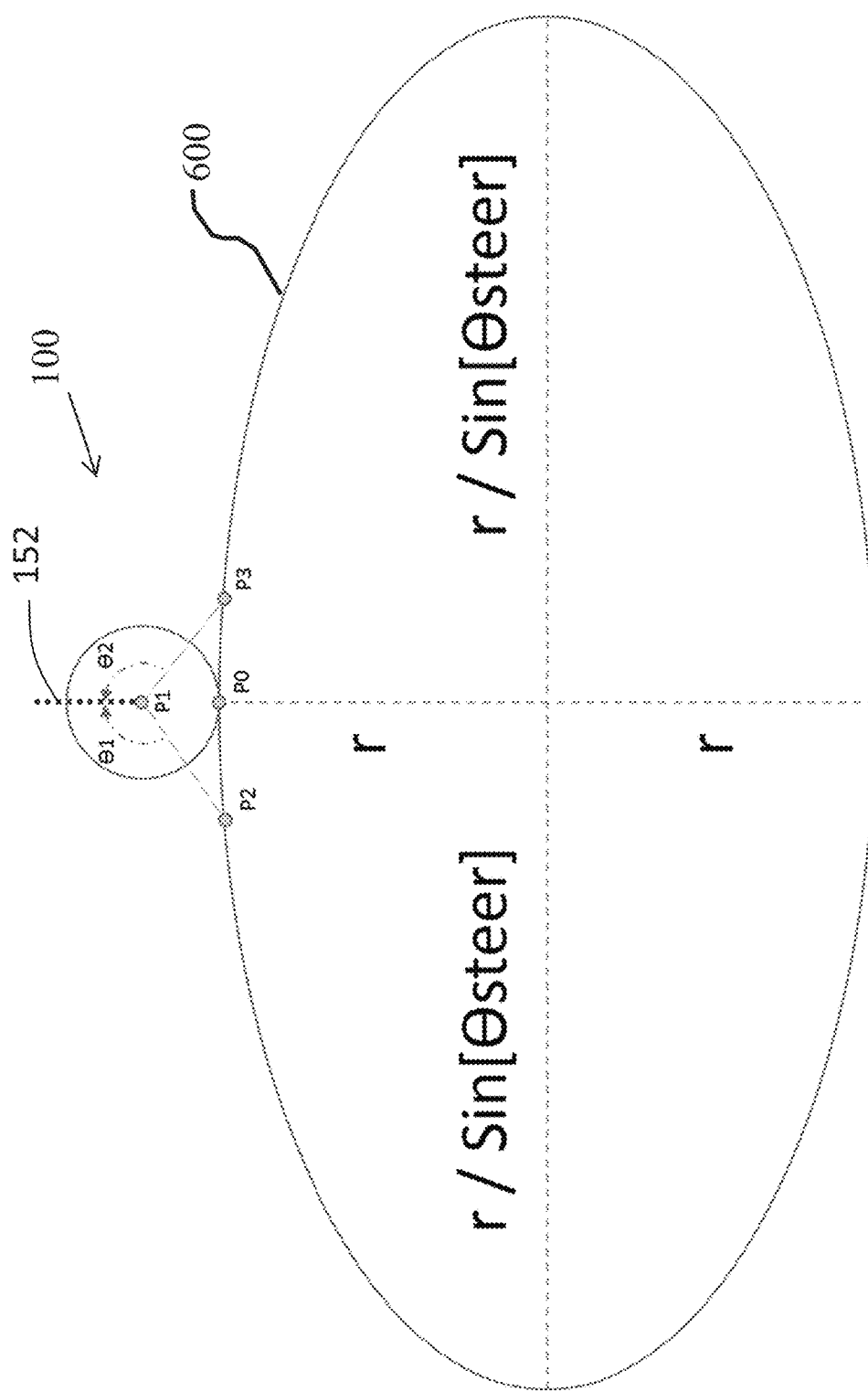

FIG. 4 is a perspective-view diagram of a magnetic robotic crawler vehicle in accordance with one or more disclosed embodiments; and FIG. 5 is a perspective-view diagram of a sensor probe assembly of a magnetic robotic crawler vehicle in accordance with one or more disclosed embodiments; and FIG. 6 is a side-view of a simplified schematic model of a robotic vehicle 100 traversing a pipe in accordance with one or more disclosed embodiments.

DETAILED DESCRIPTION OF CERTAIN EMBODIMENTS OF THE INVENTION

By way of overview and introduction, a compact magnetic robotic crawler vehicle having anti-rocking supports is disclosed. The vehicle is configured to be capable of traversing ferromagnetic surfaces of almost any curvature with high dexterity and maneuverability regardless of surface geometry and orientation.

According to an aspect of the invention, the vehicle is comprised of a main chassis section including a magnetic drive wheel configured to drive the vehicle along a surface and steer the vehicle. More specifically, the magnetic wheel is an assembly that is generally comprised of axially magnetized hub comprising magnetized disks or rings (hereinafter referred to as the "magnetized hub") extending axially between two ferromagnetic flux concentrator yokes having symmetrical size and provided at the two ends of the magnetized hub. According to a salient aspect of one or more of the disclosed embodiments, the magnetized hub includes a central chamber section that is configured to house an inspection probe therein (i.e., within the chamber) and is made from a material having a high magnetic permeability. In other words, the chamber is designed with a dual purpose, namely, to host the sensor(s) and actuators while also minimizing low magnetic permeability regions along the magnetic flux lines that extending through the hub and the yokes. For instance, as further described herein, the chamber can be constructed from a ferromagnetic material and designed to avoid saturation of the chamber and leakage of flux.

In some configurations, the sensor can be a roller sensor probe configured to roll along a pipe surface and take sensor measurements. Furthermore, the probe is preferably supported by the chassis using a vertically oriented spring loaded mechanism providing for self-adjustment of the probe position within the chamber in the up/down direction relative to the surface. Accordingly, the chamber has at least an open bottom (e.g., the side facing the pipe surface) such that the probe can be held against, or close to, the surface during operation and move upward and downward depending on the contour of the surface being traversed and inspected.

According to a further salient aspect, a stabilization mechanism is also attached to the chassis. The stabilization mechanism comprises front and rear facing support elements (e.g., extending perpendicularly to the axis of the drive wheel) that serve to minimize rocking of the chassis about the axis of the drive wheel. With respect to the stabilization mechanism, the front and rear support elements are generally aligned along the longitudinal axis of the crawler. Preferably, the support elements are also moveable relative to the chassis. In some configurations the support elements can be mechanically coupled such that they move in unison relative to the chassis. The up and down movement of the stabilization mechanism can be assisted by a spring that passively adjusts the height of the support elements depending on the curvature of the surface. The spring assisted stabilization mechanism serves to maintain the front and rear support elements against the traversed surface and, thus, maintains the chassis crawler in an ideal upright position on the surface, as long as one or more of the support points contact the pipe. In some configurations, the support elements can be configured to move in unison relative to one another, for instance, the two support elements can be coupled together with spur gears and the mechanism is spring loaded such that the two support elements move relative to each other even amounts as the curvature of the traversed surface changes. In some implementations, magnets can be provided at (or near) the front and rear support contact points to help prevent the robot from detaching from the pipe. In addition, in some implementations, one or more sensors can be provided at the front and rear contact points, for instance, to detect contact with the pipe and detect undesired tilt of the robot.

The foregoing aspects of the crawler and, as further described herein, address multiple major challenges that are common in the development of inspection crawlers while simultaneously reducing the overall size and weight of the inspection vehicle.

Figure 1A:
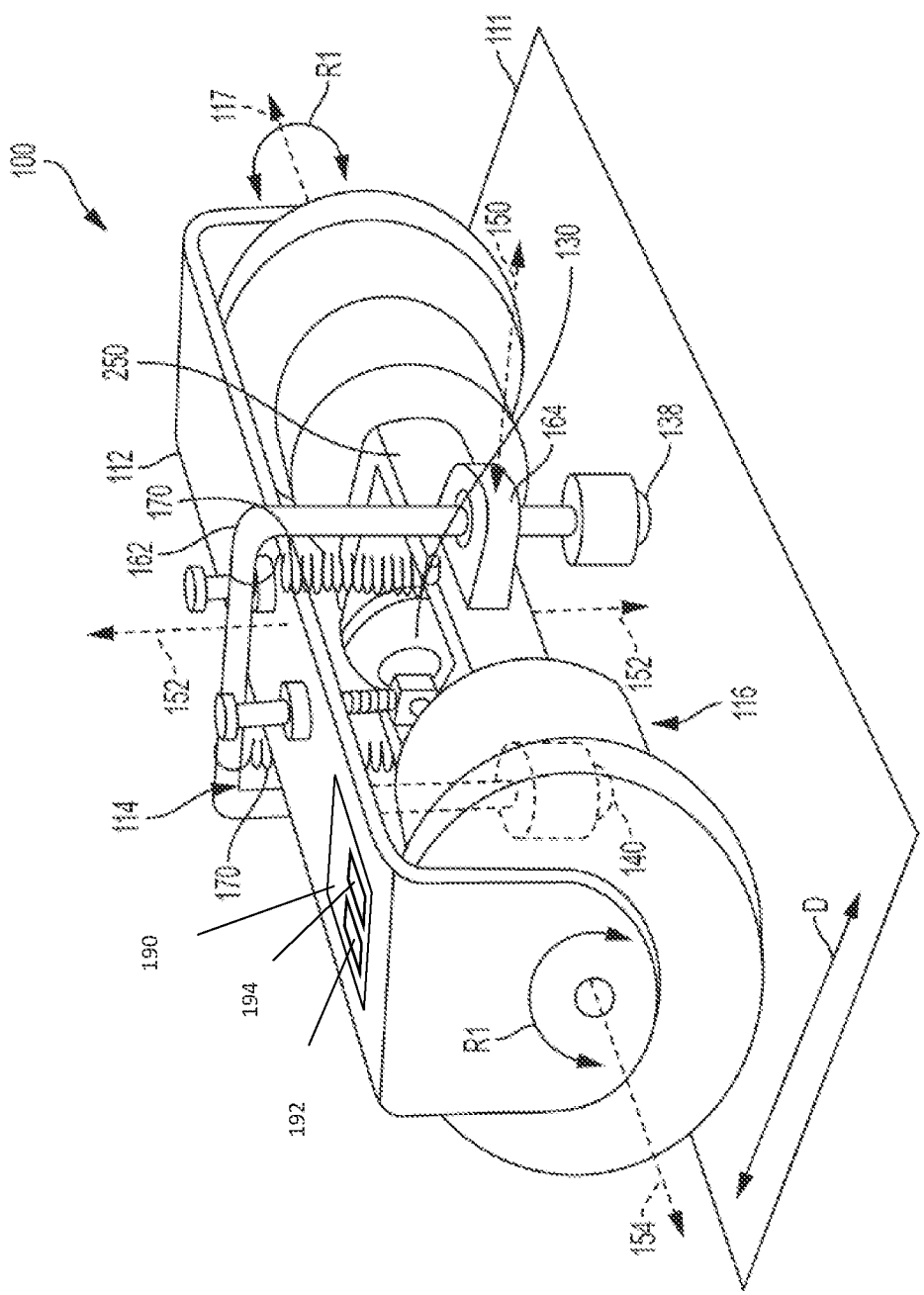
FIG. 1A is a perspective-view diagram of a magnetic robotic crawler vehicle in accordance with one or more disclosed embodiments.

Referring to FIG. 1A, an exemplary robotic vehicle 100 in accordance with an embodiment of the invention is shown from a rear and side perspective view. As shown, the vehicle can be in the form of a magnetic crawler inspection vehicle (such as a robot as shown herein) that can be controllably driven across the surface 111. For example, the vehicle 100 can be a robotic device for inspection of one or more regions of the surface 111 using one or more on-board sensor probes that can be controlled by a user who can transmit control commands to the vehicle to control the operation of the vehicle. In this manner, the user can effectively drive the vehicle across the surface and can stop and steer the vehicle as well. The vehicle can also be configured to drive autonomously as well.

The robotic vehicle 100 includes a first chassis section 112. A magnetic drive wheel 116 is connected to the first chassis section 112. Also connected to the first chassis section 112 is a stabilization mechanism 114, comprising a front support element 140 (not shown) and a rear facing support element 138. As noted, the drive wheel is magnetized so as to allow the robotic inspection vehicle 100 to magnetically attach to a ferromagnetic metal surface 111, such as a metal pipe or metal storage tank and be movable thereacross. Thus, the first chassis section 112 provides the means for moving the vehicle 100 across the surface 111, while the front and rear support points passively lead and follow the first chassis section while moving. It should be appreciated that, as further described herein, the front and rear support elements can each comprise an assembly including one or more wheels, for instance, magnetic wheels, sensor probe wheels.

In the robotic vehicle's forward and rear-ward direction of travel, which is indicated by arrow "D," the drive wheel 116 of the robotic vehicle rotates about its axis 154 in either direction indicated by arrow "R1" in response to a motor that propels the vehicle forward and backwards. The axis of rotation 154 of the drive wheel is also referred to as the lateral axis 154, which runs widthwise through the first chassis section. Perpendicular to the lateral axis and extending lengthwise through the middle of the first chassis section (e.g., parallel to a flat surface that the crawler is on and bisecting the vehicle into left and right sides/halves) is the longitudinal axis 150. Also shown in FIG. 1A is the perpendicular axis 152, which extends perpendicularly to both the longitudinal axis and the lateral axis and is normal to the surface 111 (when the crawler is resting on a flat surface).

It can also be appreciated that the drive wheel can be configured to propel the vehicle in the forward and rearward direction as well as steer the vehicle, as further described herein. It can be further appreciated that the drive wheel provides stability to the vehicle 100. In particular, the drive wheel can include a strong magnet which creates a pull force between the wheel and a ferromagnetic surface 111 on which the vehicle can be moved, and this structural arrangement assists in resisting tipping of the vehicle. In addition, the drive wheel can have a relatively wide stance, which further provides stability to the vehicle by resisting rolling or tipping about the longitudinal axis 150.

Although not shown, the first chassis section can include a control module. The control module can include a motor, a drive assembly for transferring mechanical power from the motor to the drive wheel 116, a power source (e.g., battery), and a controller 190 that, using a processor 192, can control the operation of the vehicle by processing sensed data, processing stored instructions, and/or processing control instruction/signals received from a remote computer/operator (not shown). The first chassis section 112 can also further include other operating parts including a steering mechanism.

Drive Wheel

Figure 1B:
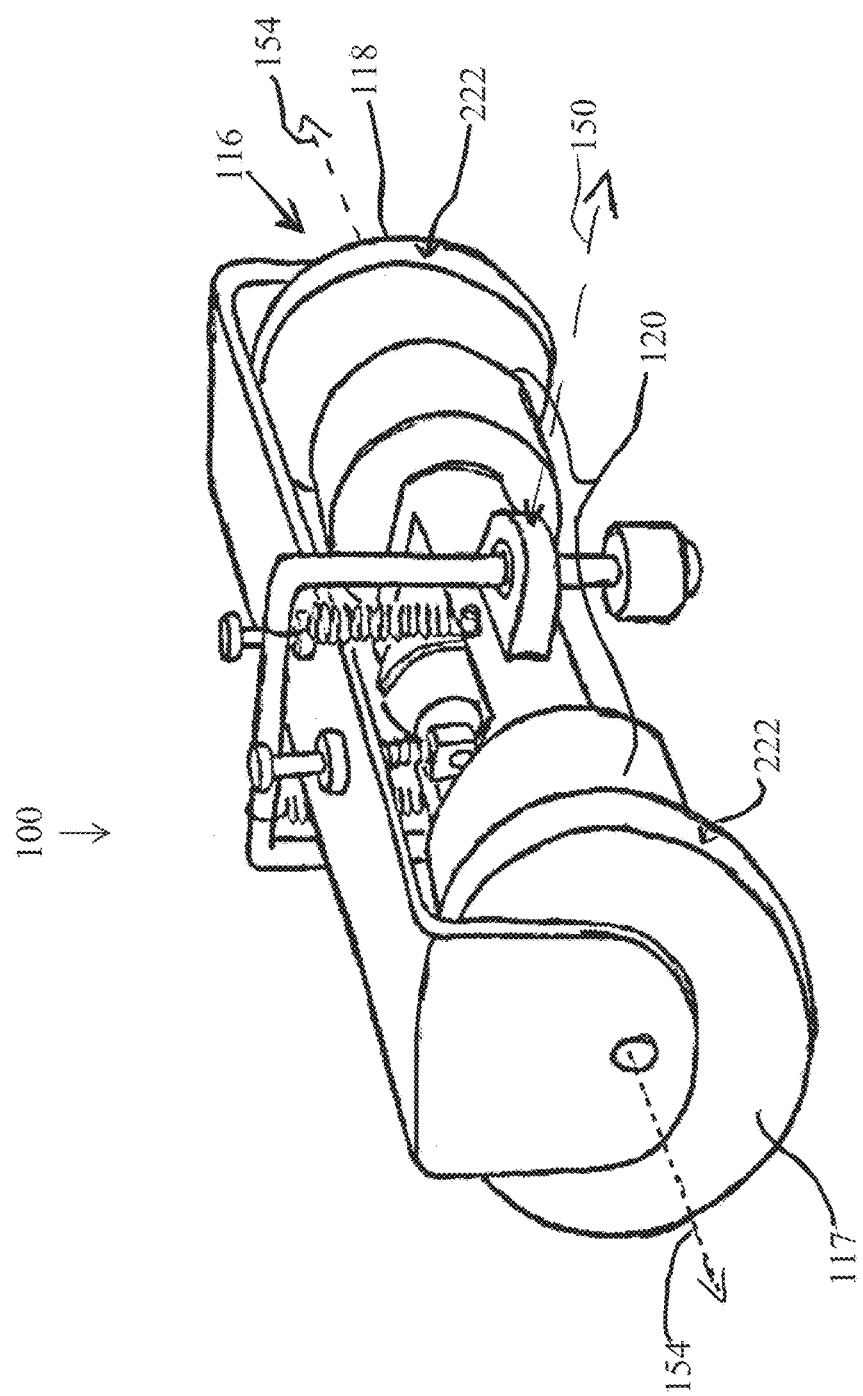
FIG. 1B is a perspective-view diagram of the magnetic robotic crawler vehicle of FIG. 1A in accordance with one or more disclosed embodiments.

FIG. 1B depicts the same vehicle 100 as FIG. 1A and highlights components of the drive wheel 116 that is configured to propel and can steer the vehicle 100. In some implementations, the drive wheel 116 can comprise a magnetic wheel assembly including two spaced apart steel yokes, namely, a left yoke 117 and a right yoke 118, which are configured to act as magnetic flux concentrators. The magnetic drive wheel 116 can also include an axially magnetized cylindrical hub 120 extending between the two yokes.

Additionally, although not always required, the yokes 117 and 118 are preferably configured to be independently driven so as to be able to rotate the two yokes differentially and thus achieve full maneuverability of the vehicle 100. For instance, in some implementations, an angular contact bearing (not shown) sitting between a non-rotating end of the magnetized hub 120 and a rotating yoke is one exemplary way of achieving independent rotation. Other possible configurations are envisioned, such as combining needle thrust bearings with regular ball bearings (also not shown). Preferably, the bearing seat is configured to have the smallest possible airgap between a rotating steel yoke and the adjacent side face of the magnetized hub and also to maximize the overlap between the magnetized side face of the hub and the portion of the steel yoke positioned across the air gap from it, this is in order to maximize the resulting pull force of the magnetic wheel.

A configuration that allows one or more of the yokes of the drive wheel 116 to rotate freely is useful when pivoting in place on the surface 111. Such an arrangement allows rotation about truly a single point (e.g., the point of contact between the surface and the left or right yokes, P0L and P0R, respectively) rather than the mid-point of the axle of the driving wheel (e.g., the intersection of axis 152 and the axis of rotation 154). This arrangement can also prevent the driving wheel from damaging the surface as it slides through the rotation. Accordingly, the drive wheel 116, and thus the robotic vehicle 100, can be controllably steered in any number of directions along the surface 111 including, for example and without limitation, circumferentially, longitudinally, in a helical path and the like. Although the yokes are shown as having a flat rim profile 222, the yokes can also have a curved rim profile such that each yoke contacts the surface at just one point regardless of the surface's curvature. In some implementations, the rim can be knurled and/or textured or coated to provide grip. Such an arrangement can improve the consistency of pull force and friction and can also improve the performance of the drive mechanism and reduce the power consumption of the drive wheel when pivoting.

Figure 2A:
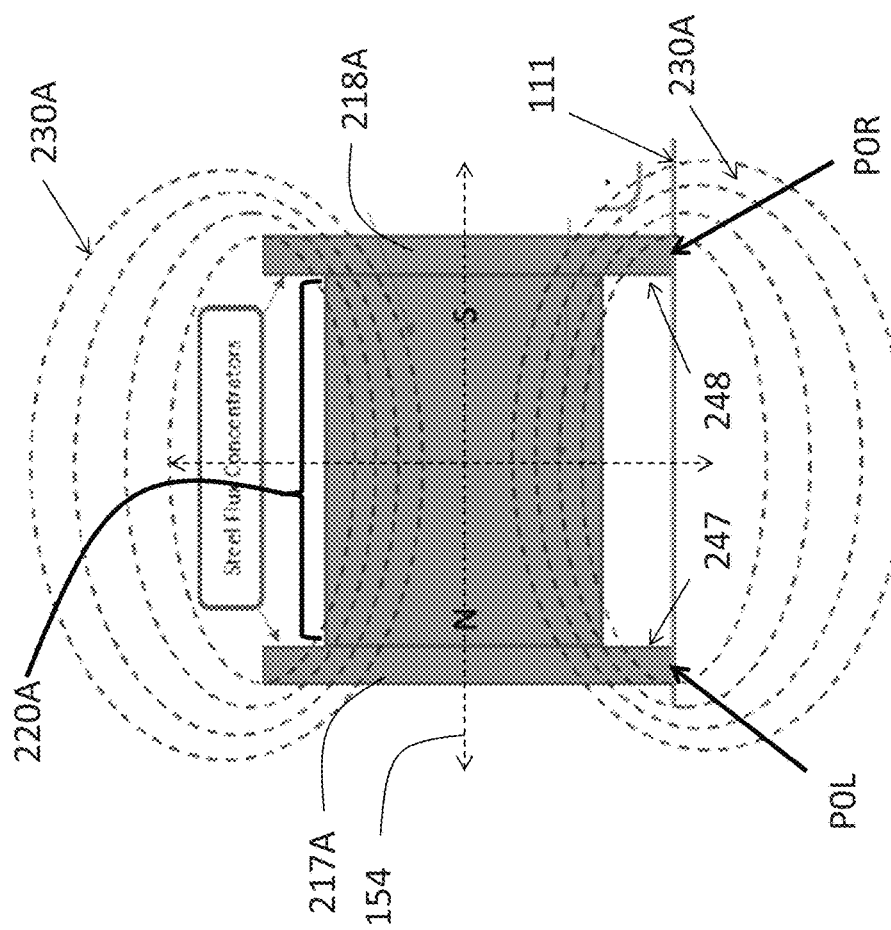
FIG. 2A is a rear-view conceptual diagram of a magnetic drive wheel in accordance with one or more disclosed embodiments.
Figure 2B:
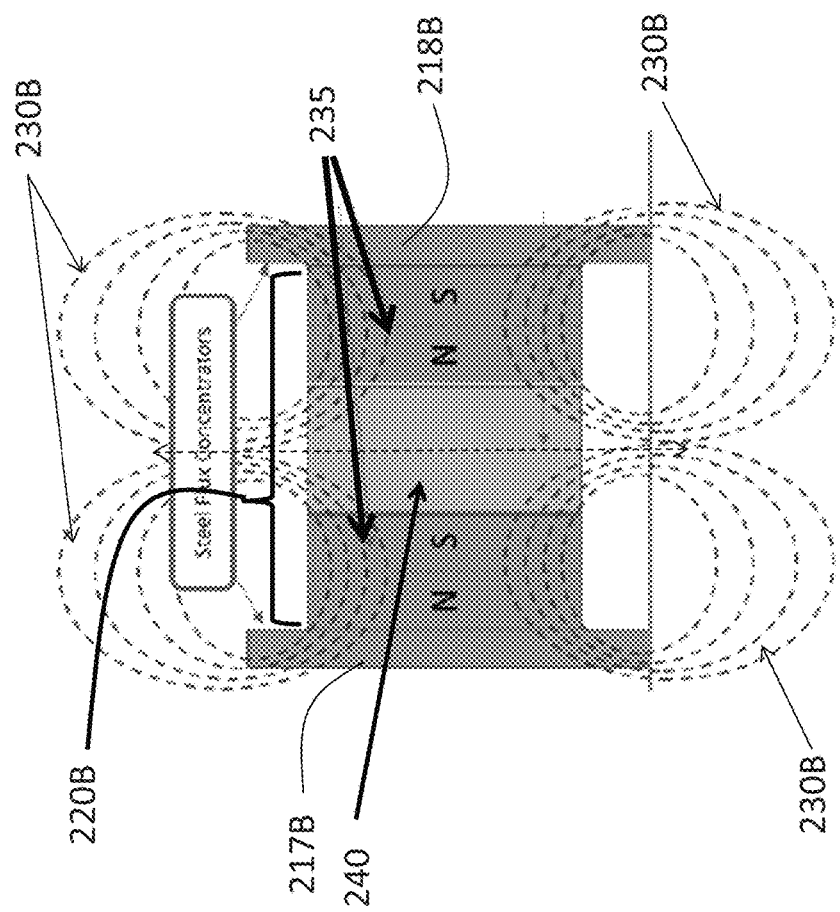
FIG. 2B is a rear-view conceptual diagram of a magnetic drive wheel in accordance with one or more disclosed embodiments.

FIG. 2A-2C are conceptual diagrams of exemplary drive wheel assemblies, in accordance with one or more embodiments of the invention. For simplicity, FIGS. 2A-2C are shown from a rear (or front) view and are simplified in that they do not depict a first chassis section or a stabilization mechanism. The main differences between the exemplary drive wheel configurations depicted in FIGS. 2A-2C concern the design and construction of the axially magnetized hub extending between the yokes, as further described herein.

FIG. 2A depicts a basic configuration of an axially magnetized cylindrical hub 220A, as would be understood by those in the field of magnetic wheels. In such a configuration, the cylindrical hub comprises an axially magnetized magnet 225, which can comprise one or more disc, cylinder or ring magnets. The magnet is axially magnetized because the magnetization direction is along the axis of the magnet which, as shown, is aligned with the rotational axis/lateral axis 154. Accordingly, the north and south poles of the magnet, which are located at the end faces of the magnet, are adjacent to the inner surface 247 of the left yoke 217A and inner surface 248 of the right yoke 218A, respectively. As shown in FIG. 2A, the yokes and serve to concentrate the magnetic field such that it follows the path generally illustrated by the magnetic flux loops 230A that loop continuously through the magnet 225, the yokes at both ends thereof, and return through a medium (e.g., the surface 111 in contact with the yokes). Such a configuration provides a relatively high attractive force between the magnetic wheel assembly and the surface.

It should be noted that in applications using magnetic wheels it can be desirable to have available physical space in the central region of the wheel for placement of actuators or sensors, however, introducing empty space requires the removal of magnetic material which naturally reduces the pull force of the wheel by the removal of the magnetic material plus disruption of the flux of the remaining magnetic material by forcing flux lines to flow through air or other materials having low magnetic permeability. FIG. 2B illustrates an exemplary configuration in which the cylindrical hub (e.g., hub 220B) includes a central section 240, which defines an open space near the midpoint between the left yoke 217B and right yoke 218B. Also shown are multiple axially magnetized magnets 235 disposed between the left side of the central section and the left yoke and between the right side of the central section and the right yoke. As noted, the magnets can be one or more disc, cylinder or ring shaped magnets. FIG. 2B also illustrates the disrupted magnetic field(s) following along the paths generally illustrated by the magnetic flux loops 230B, which each loop through half of the magnetized hub a respective yoke and the medium (e.g., the surface in contact with the yoke). As noted, such a configuration can provide a relatively weaker attractive force between the magnetic wheel assembly and the surface.

In accordance with one or more embodiments of the invention, FIG. 2C is a conceptual diagram illustrating the exemplary configuration of the axially magnetized cylindrical hub 120 of vehicle 100 shown in FIG. 1A. As shown, the extending axially between the left yoke 117 and right yoke 118 and that includes a central housing 250 defining an open chamber for housing an inspection probe 130 therein. According to a salient aspect, the housing 250 is specifically configured to house the inspection probe at least partially within the open space defined by the exterior walls of the housing, while also minimizing low magnetic permeability regions along the magnetic flux lines that preferably extend continuously through the hub and the yokes.

More specifically, in one or more embodiments, the cylindrical hub 120 includes a plurality of axially magnetized magnets, which can be in the form of one or more disc, cylinder or ring magnets. As shown in FIG. 2C, two magnets 260L, 260R are provided, although more or fewer magnets can be used. Magnet 260L is disposed between a left side of the housing 250 and the inner side surface 277 of the left yoke 117. Magnet 260R is disposed between a right side of the chamber and the inner side surface 278 of the right yoke 118. As noted, the yokes serve to concentrate the magnetic field. In addition, because the yokes 117 and 118 are preferably independently rotatable while at least the housing portion 250 is preferably not rotating (e.g., to keep the probe 130 consistently positioned relative to the surface 111), the yokes can be configured to rotate independent of one or more portions of the hub. For instance, as noted bearings configured to minimize the air gap (i.e., distance) between a rotating component of the wheel and an adjacent stationary component can help to maximize the resulting pull force of the magnetic wheel.

In some implementations, the housing 250 can be integrally formed with one or more of the magnets. In addition or alternatively, the housing can be a separate structure. In cases where the housing is a separate structure an end of the housing can be fixedly coupled to an adjacent magnet such that the joined housing and magnet do not move relative to one another. In addition or alternatively, an adjacent magnet (or yoke) can be configured to rotate relative to the stationary housing. Alternative magnetic wheel configurations are possible, for instance, the housing can be adjacent to one or more of the yokes, rather than being positioned between two magnets. In such a configuration, the one or more magnets can be coupled to the yokes at another location, for instance, the opposite side of the yokes.

As noted, the housing 250 can be specifically configured to minimize low magnetic permeability regions along the flux lines. In some implementations, this is achieved by constructing the housing using a ferromagnetic material. Moreover, the particular shape of the open chamber defined by the housing can be configured to avoid saturation of the chamber and leakage of flux. Accordingly, as shown in FIG. 2C, the magnetic field generated by the magnets and passed through the central housing 250 and concentrated by the yokes 117 and 118 into the surface 111 can follow the path generally illustrated by the magnetic flux loops 230C, which continuously through the length of the magnetized hub 120 and each yoke and through the medium (e.g., the surface 111 in contact with the yokes). It should be understood that the magnetic flux lines illustrated in FIGS. 2A-2C are simplified and shown merely for basic illustrative purposes. The particular way that the magnetic field behaves in practice can depend strongly on many variables including the dimensions of the housing and the open chamber, the distance between the magnet rings and the target surface and the like.

Figure 3A:
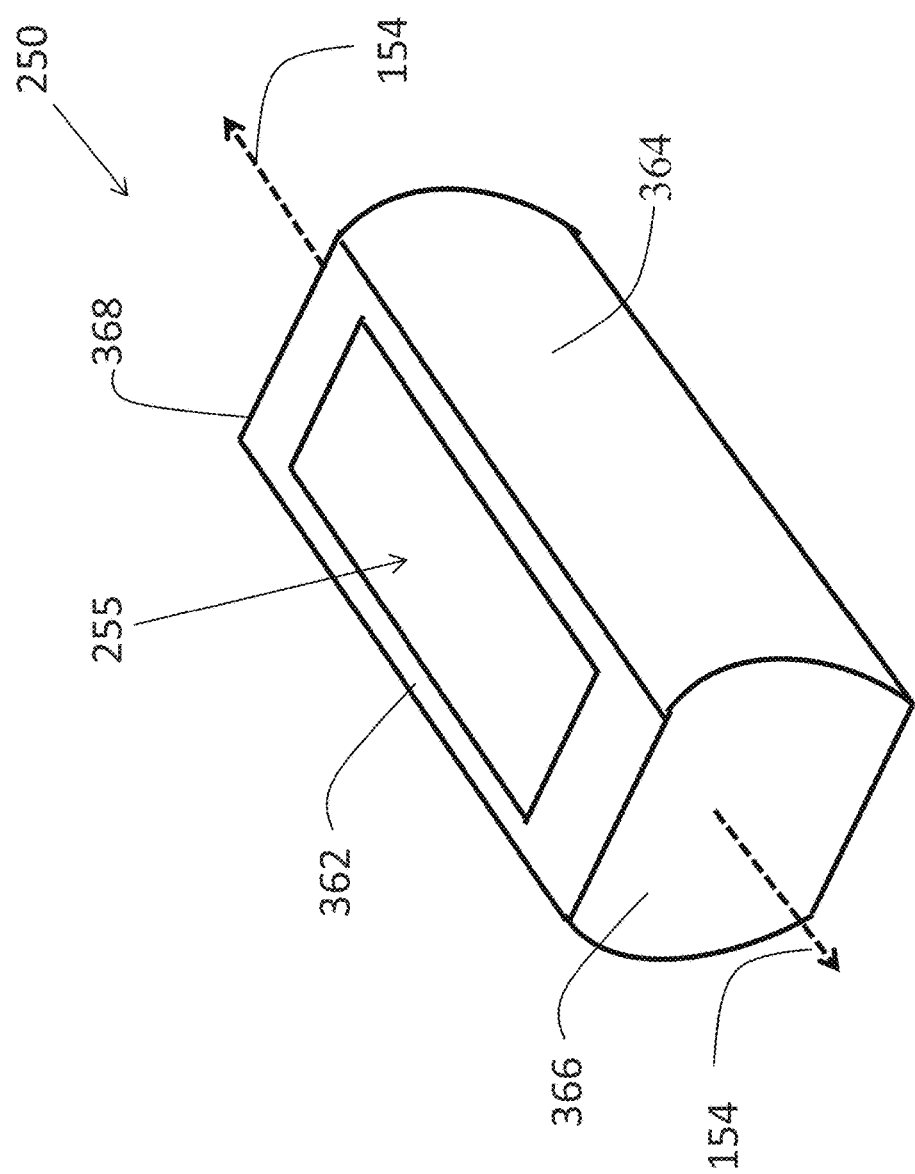
FIG. 3A is a perspective-view diagram of a housing component of the magnetic drive wheel of FIG. 1A in accordance with one or more disclosed embodiments.
Figure 3B:
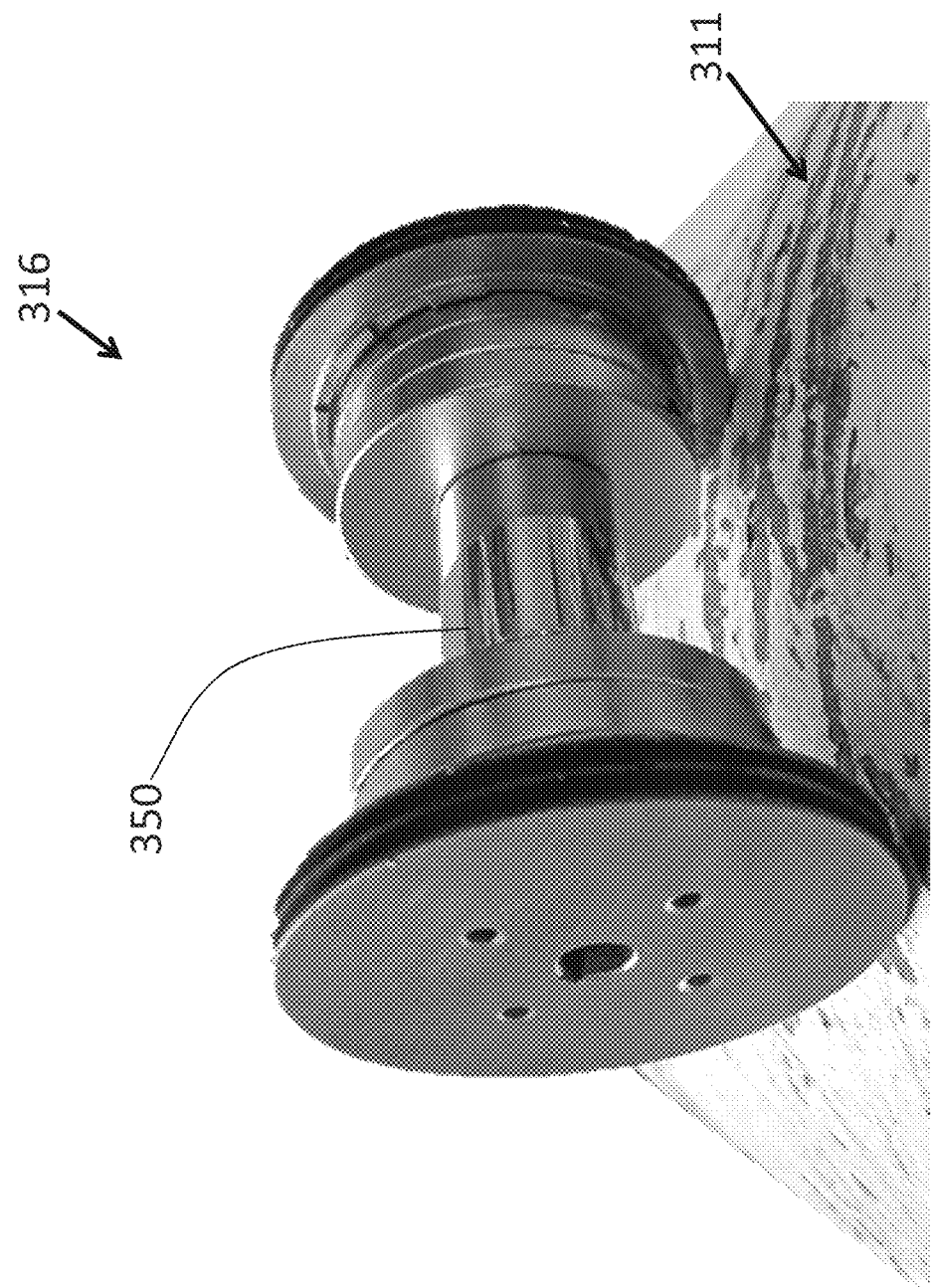
FIG. 3B is a perspective-view diagram of a magnetic drive wheel in accordance with one or more disclosed embodiments.

FIG. 3A is a perspective view of an exemplary configuration of the central housing 250 in accordance with one or more embodiments. The housing 250 is an elongate structure extending generally in the direction of the axis 154. The housing 250 is shaped to define an open chamber 255 and configured to house one or more actuators and/or sensor probes (e.g., probe 130) therein. In the particular configuration shown in FIG. 3A, the housing 250 has an open bottom side, which preferably faces the inspected surface, and an opposing open top side such that the hollow interior chamber 255 extends entirely through a portion of the housing in the up and down direction. The housing can thus be defined by a pair of opposing lateral walls, namely, the front wall 362 and back wall 364, which extend between a left end-wall 366 and right end-wall 368, and thereby defining the open chamber 355. It should be appreciated that although the exemplary housing 350 is shaped like a hollow cylinder extending along the axis of rotation 154 with openings provided in a top side and opposing bottom side, the housing can have any number of different shapes. For instance as shown in FIG. 3B, which is a perspective view of an exemplary drive wheel 316 having spaced apart yokes, an axially magnetized hub that includes a central housing 350. As shown, for example, the housing can have the form of an elongate structure (e.g., a hollow cylinder) having an open bottom side (not shown). Alternative housing sizes and shapes can be used as well.

Returning to FIG. 3A, the housing 250 can be configured to house a probe within an open chamber therein, while still enhancing the overall magnetic pull force of the crawler on the pipe by creating a single continuous pathway of high magnetic permeability material for magnetic flux to flow through. Preferably, the housing is constructed using a material having high magnetic permeability, such as a ferrous material. The housing can also be configured to minimize low magnetic permeability regions between the ends of the housing and the adjacent component(s) of the magnetic drive wheel assembly (e.g., magnets or flux concentrating yokes that are adjacent to a respective end of the housing). As noted, minimizing the air-gap distance between the ends of the housing and the adjacent magnetic wheel components can improve the magnetic permeability of the housing. Increasing the area of the hub that faces the magnetic field source (be it the yokes or the magnet itself depending on the arrangement) can also help the hub carry more magnetic flux therethrough. Accordingly, providing end-walls having a sufficient surface area facing the adjacent wheel components can also maximize the overlap between the magnetized side face of the hub and the portion of the steel yoke positioned across the air gap from it thereby increasing the magnetic saturation point of the hub 120.

Moreover, the size, shape and thickness of the one or more sidewalls (e.g., walls 364 and 362) extending between the end walls 368 and 366 can be defined to improve the magnetic permeability of the housing 250, for instance, by having a sufficient thickness and shape that facilitates axially magnetizing the housing. In some embodiments, the overall magnetic permeability of the housing can be further improved by minimizing the volume of the open chamber 255, which is an area of relatively lower magnetic permeability. For instance, the walls of the housing can be constructed to provide a chamber that is as small as possible while still housing the elements necessary to allow for the desired motion of a probe 130 during operation. Avoiding the use of non-ferrous materials within the chamber, to the extent possible, can also be beneficial.

Ultimately, the exemplary configuration of the cylindrical hub 120 and housing 250 shown in FIGS. 2C and 3A provide a relatively high attractive force between the magnetic wheel 116 and the surface 111, while still providing a central chamber that is suitable for housing a probe 130 at least partially therein.

It should be noted that the exemplary crawler vehicle 100 illustrated in FIG. 1A and further described herein preferably includes a cylindrical hub 120 and housing 250 as shown and described in relation to FIGS. 2C and 3A, however, alternative hub configurations can be utilized, for instance, the hub configurations shown and described in relation to FIGS. 2A and 2B and 3B.

Stabilization Mechanism

Turning now to FIG. 1A, the stabilization mechanism 114 can include a front support element 140 provided in-front of the first chassis section 112 and a rear support element 138 provided behind the first chassis section (assuming that the vehicle 100 is traveling in the direction identified by the arrow D). The support elements can be configured to limit the amount that the first chassis section can pitch forward or backwards about the axis 154 of the drive wheel 116, thereby maintaining the chassis in an upright and, more preferably, normal position, relative to the surface.

In some configurations, the front and rear support elements are centered, e.g., in line with the longitudinal axis 150 that extends through the middle of the vehicle 100. However, alternatively, the front and rear support elements can be offset from the vehicle's longitudinal centerline.

The support elements can, for example and without limitation, comprise a passively rolling ball-caster. Alternative support element configurations can be utilized, for instance, a wheel rotating about a fixed rotational axis that is parallel to the rotational axis 154 of the drive wheel. By way of further example, a support element can comprise a piece of rigid smooth plastic configured to slide along the surface 111. In such a case, preferably, a material having a low coefficient of friction can be used to facilitate the sliding of the front support and help prevent scratches on the surface. In addition, magnets can also be provided along with the support elements, for instance, behind or around each support element so as to assist in maintaining contact with the surface. In addition, sensors can be provided at the front and rear contact points so as to detect contact between respective support elements and the pipe and detect undesired tilt of the robot. This information could be used by the crawler for various purposes, for example, to trigger an alarm warning the operator of undesired tilt.

As noted, the support elements are preferably moveable relative to the first chassis section 112. For instance, in the exemplary configuration shown in FIG. 1A, the stabilization mechanism 114 can include a linking structure 162 having the shape of an upside down 'U,' wherein the first and second support elements 138 and 140 are joined at respective ends of the vertically oriented shafts of the linking structure. In addition, the linking structure 162 can be moveably coupled to the chassis 112 and/or the drive wheel 116 such that the support elements can move relative to the chassis and/or wheel in one or more directions. For instance, FIG. 1A shows the linking structure 162 including front are rear shafts that are slidably mounted to the cylindrical hub 120 using a rear linear bearing 164 and a front linear bearing (not shown) that are attached to the front and rear side of the housing 250. Accordingly, the shafts of the linking structure can slide linearly through the bearings in the up and down directions (e.g., in the direction of axis 152) and thus moving the front and rear support elements up and down relative to the surface 111.

Although the up and down movement of the support elements 138 and 140 provided by the stabilization mechanism 114 is generally passive, the movement can be biased or assisted using tensioning springs and the like so as to maintain the support elements in contact with the traversed surface during operation. For example and without limitation, FIG. 1A depicts two tensioning springs 170 that are each attached at one end to the cylindrical hub 120 and attached at the other end to the linking structure 162. The spring tension applied between the drive wheel, which is planted on the surface 111, and the sliding linking structure 162 serves to maintain the first and second support elements 138 and 140 in contact with the surface 111, by effectively pulling the linking structure towards the surface during operation.

It can be preferable to configure the stabilization mechanism such that the downward force exerted by the stabilization mechanism does not overcome the magnetic force that maintains the drive wheel in contact with the traversed surface. Alternatively, in a further aspect, strong permanent magnets could be added in close proximity to the support elements 138 and 140 such that they remain in contact with the traversed surfaced either completely due to the magnetic force or by a combination of magnetic force and force exerted from the crawler chassis. In either case, even if the magnets just offset a part of the force required for contact, the crawler will be less likely to detach from the surface.

Moreover, although the downforce applied by the stabilization mechanism on the front and rear support elements assists in maintaining the support elements against the surface so as to keep the vehicle stable, it can be appreciated that in some instances this downward force can be overcome, thereby causing one or more of the support elements to break contact with the surface. For instance, in the case of traversing an obstacle on the surface, the front support element 140 can contact the obstacle, which offers some initial resistance until the downward force of the stabilization mechanism 114 is counteracted thereby causing the front support to temporarily detach from the surface and the vehicle to rock back about the axis of the magnetic wheel and, thus, allowing the front support to overcome the obstacle.

It should be noted that in the embodiment shown in FIG. 1A, the anti-rocking support elements move in parallel linear directions and are coupled mechanically so as to move together. In addition or alternatively, the support mechanism can also be configured to provide for movement of the front and rear support elements at an angle relative to one-another. In addition or alternatively, the front and rear support elements can be configured to move independently. Moreover, the support elements can be configured to have a degree of independent movement and a certain degree of linked movement.

In addition to using a stabilization mechanism that allows the front and rear support elements to move in unison relative to the chassis 112 and/or drive wheel 116, the stabilization mechanism can also be configured to allow the front and rear support elements to also move relative to one another. FIG. 4 depicts an exemplary configuration of a vehicle 400 including a stabilization mechanism 414 that moveably supports a front support element (not shown) and rear support element 438. In particular, the stabilization mechanism includes a front facing linking structure 462 and a rear facing linking structure 464 that each have an elongate C shape. The rear facing support element 438 and front facing support element (not shown) are mounted near the midpoint of the front and rear facing linking structures, respectively. The ends of the front and rear facing linking structures can be pivotally mounted to the left side wall 482 and the right side wall 484 of the first chassis structure 412. In addition, the front and rear linking structures can be mechanically coupled together, such that the linking structures are configured to pivot about respective pivot points in concert. For example, interlocking spur gears 466 and 468 can, respectively, be coupled to the ends of linking structures 462 and 464, which are pivotally joined to the chassis 412. Pivoting linking structures that are coupled using complementary spur gears allows the front and rear support elements to move in an up and down direction relative to the first chassis section but along a slightly curved path as indicated by arrows P1 and P2, respectively. Thus, the movement is not limited to only the up and down direction relative to the chassis but can include a curved path in which the support elements also move closer or further apart from one another.

As a result of the particular geometry of the linking structures and pivot points defining the stabilization mechanism 414, the front and rear support elements are moveable relative to first chassis section 112 along arcs P1 and P2 in order to maintain the front and rear support elements in contact with the surface 111, even as the curvature of the traversed surface changes. For instance, the self-adjusting stabilization mechanisms allow the vehicle 400 to traverse pipes having a wide range of diameters and in any direction.

Although the up and down movement of the support elements provided by the stabilization mechanism 414 is generally passive, the movement can be biased or assisted using one or more tensioning springs. For example and without limitation, FIG. 4 depicts a tensioning spring 470 extending between the front and rear facing linking structures 462 and 464. The spring tension applied between the two linking structures can assist in maintaining the front and rear support elements 440 and 438 in contact with the surface 111, by effectively pulling the linking structures towards one another during operation.

As noted, mechanically coupling the anti-rocking stabilization elements such that they move symmetrically relative to the chassis and, optional, relative to one-another, can minimize undesired tilt/rocking of the crawler due to force misbalance and maintains uprightness of the crawler on curved surfaces regardless of the radius of curvature (e.g., size of the pipe) or the orientation and position of the crawler on the surface, provided that the stabilization elements contact the pipe.

The exemplary stabilization mechanisms are provided as non-limiting examples. Other stabilization mechanism configurations and other systems and methods for providing downward force on front and rear stabilizing elements can be used without departing from the scope of the disclosed embodiments. In addition, actuators such as linear actuators and motors acting instead of or in addition to the spring-like elements mentioned above can be utilized to force the front and rear support elements down against the surface being traversed.

While the embodiment shown in FIG. 1A illustrates the anti-rocking support elements moving independently of the probe, alternatively, the stabilization mechanism 114 can be mechanically linked to the probe assembly and configured to maintain a prescribed relationship between the motion of the probe, as further described below, and the motion of the support elements. Such a configuration can be beneficial in applications where the geometry of the vehicle 100 and the contour of the surface 111 can require the support elements and the probe to move at different rates to achieve normalized orientation of the probe and/or vehicle relative to the surface. In one exemplary configuration, a cam can be coupled to the stabilization mechanism and a cam follower can be attached to the probe. Moreover, the profile of the cam can be defined such that the follower drives the DCP up and down according to a prescribed non-linear relationship that maintains the probe in contact with the pipe. In addition, the prescribed non-linear relationship can be a function of the curvature of the surface (e.g., a pipe) and/or the orientation of the device on the surface.

Probe Assembly

As noted, in accordance with one or more embodiments of the invention, the magnetized hub 120 can include a housing 250 that is configured to house an inspection probe within a chamber 255 with minimal disruption to the magnetic flux pathway (i.e. high magnetic permeability) across the length of the housing and hub.

FIG. 5 is a close-up rear-perspective view of an exemplary probe assembly 130 of vehicle 100 shown in FIG. 1A. The probe assembly 130 is disposed at least partially within the chamber 255 defined by the housing 250 portion of the axially magnetized hub 120. As shown, the probe assembly 130 can comprise a probe wheel 530 that rotates about a central axle 535 oriented generally parallel to the drive wheel's rotational axis 154. Accordingly, the probe wheel 530 that is configured to roll along the surface being inspected and take sensor measurements. The probe wheel can be any type of probe, for example, a dry-coupled ultrasonic wheel probe. It should however be understood that, in other applications, different types of wheeled and non-wheeled sensors could be incorporated into the probe assembly.

Furthermore, the probe assembly is preferably moveable relative to the chassis 114. For instance, FIG. 5 illustrates a vertically oriented spring loaded support mechanism referred to as a probe carrier 540 providing for self-adjustment of the probe's position within the chamber 255 in the up/down direction relative to the surface 111. As noted, the chamber 255 has at least an open bottom (e.g., the side facing the surface, not shown) such that the probe wheel 530 can be held in contact with or close to the surface during operation and can move up and down depending on the contour of the surface being traversed and inspected.

More specifically, the probe carrier 540 includes two vertical shafts 560. Each shaft is joined near one end to a corresponding end of the wheel probe's axle 535. In addition, the shafts are each moveably coupled to the chassis 112. For instance, FIG. 5 shows the shafts slideably mounted to a top wall 512 of the chassis 112 using respective linear bearings 540. Accordingly, the linear bearings enable the shafts to slide therethrough in the up and down directions.

Although the up and down movement of the probe assembly provided by the probe carrier 540 is generally passive, the movement can be biased or assisted using springs and the like. For example and without limitation, FIG. 5 depicts springs 570 that are each disposed around a length of a respective shaft 560 and compressed between the chassis section 112 and the probe assembly 130. The spring force pushing against the chassis and linearly sliding shafts serve to maintain the probe wheel 530 in contact with the surface by effectively pushing the probe assembly towards the surface during operation and self-adjusting the height of the probe wheel 530 to accommodate the curvature of the pipe and changes in curvature.

In addition or alternatively, the force maintaining the probe wheel 530 against the surface can be provided using magnets, for instance, roller wheel magnets disposed on the left and right side of the wheel 530 and rotating about the same axis as the axle 535.

With regards to this aspect of the probe assembly 130, it should be noted that placing the wheel probe in the middle of the crawler (in both a left-right direction and front-to back direction) significantly simplifies issues related to alignment of the probe against the pipe (a common issue otherwise referred to as 'normalization of the probe'). This placement of the probe basically reduces the normalization problem from a three Degree of Freedom challenge to a specific one DoF challenge where the only challenge to overcome would be the rocking of the chassis (back and forth tilt) which is addressed by the anti-rocking stabilization mechanism described herein.

Furthermore, placement of the wheel probe in the center of the crawler can eliminate issues related to the probe wheel 530 dragging sideways as it can occur in other crawlers (unless the probe is lifted off of the pipe before steering). Accordingly, the exemplary crawler vehicles disclosed herein are capable of continuously taking probe readings while carrying out any maneuver without needing to lift the probe off the pipe (i.e., by simply pivoting about the probe when steering).

The exemplary housing, probe assembly 130 and self-adjusting probe carrier 540 is provided as a non-limiting example, alternative adjustable mounting systems can be used to support the wheel probe and provide movement of the probe assembly in one or more degrees of freedom. As a further example, in some implementations, a steel housing can include an open-bottom without an open top and having a pseudo-prismatic vertical hollow region shaped to fit a spring-loaded probe carrier mounted therein wherein the tolerances between the chamber and probe carrier allow for smooth movement of the probe within the housing and through the opening while facilitating uninterrupted flow of magnetic flux axially through the housing.

With respect to the exemplary DCP probe implementation, normal contact is preferably maintained between the traversed surface 111 and the rolling sensor probe wheel 530 because a dry coupled probe generally requires its internal transducer component to be normal to the inspected surface in order to acquire a clean measurement. Thus, as noted above, in accordance with the present invention, the up/down movement provided by the probe carrier 540 and the stabilization mechanism provide passive normalization of the probe against the surface.

Moreover, the probe assembly is preferably configured to move linearly in a vertical fashion so as to compensate for different surface curvatures and the fact that the curved surface creeps (e.g., curves or crowns closer to the vehicle) in between the spaced apart wheel yokes when driving helically or longitudinally on a pipe.

Stabilization Function

The details of the exemplary vehicle 100, and more specifically the normalization and stabilization characteristics of the vehicle 100, can be further appreciated in view FIGS. 6-7, which are further discussed below with continued reference to FIGS. 1, 2C.

FIG. 6 is a side-view of a simplified schematic model of the exemplary robotic vehicle 100. FIG. 6 illustrates the geometric relationship between the main contact points between the exemplary vehicle 100 and a pipe surface. FIG. 6 further illustrates an approximation of the effective cross-section 600 of the pipe, the cross section being along the robot's middle plane as the robot traverses helically on the surface of the pipe. For simplicity, the schematic diagram only illustrates the following components:

P0 represents the contact point between the magnetic drive wheel 116 (only the circumference of the drive wheel is shown) and the traversed surface 311.

P1 represents the rotational axis 154 of the magnetic drive wheel 116.

P2 represents the contact point between the front-facing support element 140 and the surface.

P3 represents the contact point between the rear-facing support element 138 and the surface.

Θ1 and Θ2 correspondingly define the angles between the front and rear support elements and the perpendicular axis 152 of the vehicle.

As shown in FIG. 6, the effective cross section of the pipe corresponds to an ellipse. Furthermore, for a pipe of radius 'r', in the schematic, the elliptical cross section of a pipe is shown with a minor axis length of 2r and a major axis length of 2r/Sin(ΘSteer) where r represents the pipe diameter and ΘSteer represents the orientation of the crawler relative to the centerline of the pipe.

It should be noted that ΘSteer=π/2+nπ (for any integer n) corresponds to the crawler driving circumferentially around the pipe in which case the ellipse becomes a circle; furthermore, ΘSteer=0 represents the crawler driving longitudinally (i.e., lengthwise) on the pipe in which case the ellipse major axis become infinitely long. It should also be noted that the vehicle 100 includes main magnetic wheel assembly as the central element of the crawler and offers two symmetrically disposed contact points with the pipe (both represented by P0 in the side-view schematic). As such, the contact point between the pipe and the drive wheel of the crawler should typically occur along the ellipse's minor axis as shown in the diagram and not off of it (however, ΘSteer=0 and ΘSteer=π/2 are special cases in which the foregoing statement is irrelevant).

As shown in FIG. 6, the contact point between the magnetic drive wheel and the ellipse is assumed to always occur along the ellipse's major axis. That is, as the vehicle follows a constant-pitch helical path on the pipe, it does not move along the periphery of the ellipse; rather, identical elliptical cross sections constantly occur at every point as the crawler moves. This is a naturally occurring phenomenon due to the fact that the drive wheel is magnetic and that it is designed to have two symmetrically separated contact points with the surface which effectively normalize the drive wheel relative to the surface.

With respect to the stabilization mechanism 114 of vehicle 100, as noted, P2 and P3 represent contact points between corresponding front and rear facing anti-rocking support elements 138 and 140 and the pipe. Θ1 and Θ2 correspondingly define the angles between those support elements and the perpendicular axis 152 of the robot. It can thus be appreciated that variables such as gravity and torque applied to drive the vehicle can affect distribution of forces between P0, P2 and P3 and can tend to rock the chassis either forward or backwards. In other words, such forces can work to make Θ1≠Θ2. However, as long as P2 and P3 are maintained in contact with the pipe and symmetrically disposed about the crawler's mid-plane and the ellipse's minor axis, Θ1 should remain equal to Θ2 and will generally represent an upright crawler configuration in which the axis 152 is maintained normal to the pipe surface.

The foregoing principles similarly apply to implementations, in which the anti-rocking support elements pivot or rotate about an axis that is parallel to the axis of the drive wheel, for instance the exemplary vehicle 400 as shown and described in relation to FIG. 4. If anti-rocking supports that can move up/down independently are used, the uprightness of the crawler on the pipe (i.e. the absence tilt backwards or forward about the axis 154) will be a function of the relative height between the front and rear-support element.

As disclosed in connection with FIG. 1A and FIG. 4, in a preferred embodiment of the anti-rocking stabilization mechanism, the contact points P2 and P3 occur on the mid-plane of the crawler, in other words, on the plane of the 2-dimensional schematic diagram shown in FIG. 6, with P2 and P3 being symmetrically disposed relative to the ellipse's minor axis. Nonetheless, the normalizing and stabilizing function can be achieved even if the front and rear support elements were designed such that P2 and P3 contacted the pipe off of the crawler's mid plane (i.e., the plane extending through perpendicular axis 152 and longitudinal axis 150), provided, however, that they were disposed in a symmetrical fashion relative to the mid plane (i.e. equally spaced from the mid-plane on opposite sides of it). For instance, P2 and P3 could be provided closer to respective yokes of the drive wheel, which are provided near opposite sides of the vehicle, as long as the aforementioned symmetry constraint is met.
Calculating Surface Curvature and Vehicle Orientation Moreover, in accordance with one or more embodiments of the invention, the vehicle 100 can include one or more sensors 194 configured to measure the height of the probe assembly 130 relative to the chassis in the up/down direction represented by the perpendicular axis 154. Furthermore, the vehicle control computer (or an external computing device in communication with the robot) can be configured to use the measured height of the probe and the known size and shape of the vehicle (e.g., the know distance of the drive wheel yokes and position relative to the probe) to determine the pipe diameter as well as the orientation of the vehicle on the pipe. Exemplary systems and methods for calculating surface curvature and the orientation of a device are further described herein and in co-pending and commonly assigned U.S. Pat. No. 9,360,311 for "System and Method for Calculating the Orientation of a Device" to Gonzalez et. al. filed on Nov. 25, 2014, which is hereby incorporated by reference as if set forth in its entirety herein.

For instance, the control computer can determine the radius of the pipe being inspected by: causing the vehicle 100 to perform a specific maneuver, say, a 180 degree (or more) steering maneuver about the contact point of one of the two yokes; measuring the relative probe height using the sensors throughout the maneuver; capturing the highest recorded location of the probe (which occurs at the longitudinal orientation with $\Theta Steer=\pi/2+n\pi$); and calculating the radius of a circle that coincides with the wheel yokes and the probe at the recorded height based on the known distance between the wheel yokes and the probe. Furthermore, if the pipe diameter is known, a similar approach can be followed to determine the orientation of the crawler relative to the pipe centerline in real-time. In such an application, the probe height reading would preferably be correlated to an ellipse instead of a circle in order to determine the orientation.

In a further aspect, the same technique for determining the diameter of a pipe could be used to determine the diameter of a cylindrical vessel or storage tank. For instance, the crawler 100 can be deployed on the wall of the tank and it could perform the technique and multiple locations on the wall thus determining multiple measurements of the tank diameter for subsequent volume calibration purposes. In this case the sensor chamber could be fitted with a laser range finder instead of an ultrasonic testing probe to accurately measure the distance to the tank wall.

Similarly, sensors 194 can also be installed on the vehicle 100 that measure the configuration of the anti-rocking support elements (e.g., position relative to the chassis and one-another) and this information used to mathematically calculate the radius of a pipe or orientation. The relative position information of the support elements can be a supplemental or an alternative method of estimating the pipe size and vehicle orientation.

In a further aspect, parts of the crawler could be used as probing elements to take Cathodic Protection (CP) measurement readings. Cathodic Protection measurements typically involve simple voltage measurements taken between the surface of a pipe and a reference electrode mounted somewhere on the pipe itself. Because the flux concentrating yokes are made of metallic material, they can be configured to take these measurements upon contact with the pipe. For example, the crawler wheel yokes can be fitted with sensors suitable for taking voltage readings on the pipe surface, which can be referenced back to the pipe's reference electrode by an umbilical cord. In addition or alternatively, the front and/or rear support elements can be fitted with sensors that are suitable for taking cathodic protection measurements. In addition, in implementations where the crawler is deployed underwater the referencing can occur wirelessly. Moreover, for sub-sea applications the CP readings can be taken as the voltage measured between the pipe surface and the surrounding sea water and accordingly the crawler does not need to be electrically connected to the reference electrode directly.

It should be understood that various combination, alternatives and modifications of the present invention could be devised by those skilled in the art. The present invention is intended to embrace all such alternatives, modifications and variances that fall within the scope of the appended claims.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been particularly shown and described with reference to a preferred embodiment thereof, it will be understood by those skilled in the art that various changes in form and details may be made therein without departing from the spirit and scope of the invention. Therefore, the scope of the invention is indicated by the appended claims, rather than by the foregoing description. All changes that come within the meaning and range of equivalency of the claims are to be embraced within their scope.

What is claimed is:

1. A magnetic robotic crawler vehicle for traversing a surface, comprising:
   a chassis;

a magnetic drive wheel mounted to the chassis, wherein the drive wheel extends in a lateral direction and comprises:
  two spaced apart flux concentrating yokes that rotate about a rotational axis and are configured to be driven independently thereby driving and steering the vehicle along the surface, wherein a longitudinal axis of the vehicle extends perpendicularly to the lateral, rotational axis in a front and back direction and through the midpoint between the two yokes; and
  an axially magnetized hub extending laterally between the two yokes; and
a stabilization mechanism coupled to the chassis, the stabilization mechanism comprising:
  a first and a second support element configured to contact and move along the surface during normal operation of the vehicle, the first and second support elements being positioned on opposite sides of the drive wheel relative to the rotational axis, and wherein the first and second support elements are positioned symmetrically with respect to the longitudinal axis; and
  a support mechanism moveably coupling the first and second support elements to the chassis, wherein the support mechanism is configured to move the first and second support elements relative to the chassis in at least an up and down direction, wherein the up and down direction is generally perpendicular to both the longitudinal axis and the rotational axis,
  wherein the support mechanism is passive in nature and moves the first and second support elements in the up and down direction in response to a curvature of the surface thereby maintaining the first and second support elements in contact with the surface.

2. The magnetic robotic crawler vehicle of claim 1, wherein the axially magnetized hub comprises:
  one or more axially magnetized magnets; and
  a housing extending along the rotational axis,
  wherein the housing is shaped to define open chamber therein and at least one opening, wherein the chamber is provided at the midpoint between the two yokes and wherein the housing has a fixed position relative to the yokes such that the at least one opening faces downward toward the surface during normal operation of the vehicle.

3. The magnetic robotic crawler vehicle of claim 2, wherein the a housing comprises a ferromagnetic material and includes a left wall, an opposing right wall and a one or more lateral walls extending therebetween along the rotational axis, the walls of the housing being shaped to define the chamber and the one or more lateral walls being shaped to define the at least one opening therethrough.

4. The robotic vehicle of claim 3, further comprising:
a sensor probe assembly disposed at least partially within the chamber; and
a sensor support moveably coupling the sensor probe assembly to one or more of the housing and the chassis, wherein the sensor support assembly is configured to passively move the probe assembly relative to the housing in at least the up and down direction in response to the curvature of the surface thereby maintaining the probe assembly in contact with the surface.

5. The magnetic robotic crawler vehicle of claim 4, wherein the sensor probe assembly comprises:

a dry coupled wheel probe configured to passively roll generally in a direction of travel of the vehicle along the surface.

6. The magnetic robotic crawler vehicle of claim 5, wherein the sensor support comprises one or more shafts supporting an axle of the wheel probe and being coupled to one or more of the housing and the chassis by at least one mount, wherein the at least one mount is configured to allow the one or more shafts to move relative to the housing in at least the up and down direction; and
  one or more spring elements configured exert a force between at least the sensor probe assembly and one or more of the chassis and the housing, and wherein the force urges the wheel probe downward through the at least one opening of the housing and into contact with the surface.

7. The magnetic robotic crawler vehicle of claim 1, wherein the first and second support elements are equidistant from the rotational axis of the drive wheel, and wherein the first and second support elements are one or more of: positioned in line with the longitudinal axis of the vehicle, and evenly spaced apart from the longitudinal axis on opposite sides thereof.

8. The magnetic robotic crawler vehicle of claim 1, wherein the stabilization mechanism includes one or more linkages mechanically coupling the first and second support elements, wherein the one or more linkages are configured to move the first and second support elements symmetrically relative to the drive wheel in at least the up and down direction thereby maintaining the first and second support elements in contact with the surface and the vehicle substantially normal to the surface.

9. The magnetic robotic crawler vehicle of claim 8, wherein the one or more linkages are configured to move the first and second support elements symmetrically relative to the drive wheel in the front and back direction and in the up and down direction such that the first and second stabilization elements move along a respective curved path.

10. The magnetic robotic crawler vehicle of claim 8, the further comprising:
  one or more spring elements configured to exert a force between at least one of the one or more linkages and one or more of the chassis, the drive wheel and another linkage, wherein the force urges the front and rear support elements into contact with the surface thereby urging the first chassis sections into a normal position relative to the surface.

11. The magnetic robotic crawler vehicle of claim 4, wherein the stabilization mechanism includes one or more linkages mechanically coupling the first and second support elements and is configured to move the first and second support elements symmetrically relative to the drive wheel in one or more directions, wherein the stabilization mechanism is configured to maintain a prescribed relationship between the motion of the first and second support elements and the motion of the probe assembly in the up and down direction.

12. The magnetic robotic crawler vehicle of claim 1, wherein the support mechanism comprises a first linkage supporting the first support element and a second linkage supporting the second support element, wherein the first and second linkages are moveably coupled to the chassis by one or more mounts, and wherein the first and second linkages are mechanically coupled so as to synchronize the motion of the first and the second support elements in at least one direction relative to the chassis thereby maintaining the first and second support elements in contact with the surface and the vehicle substantially normal to the surface.

13. The magnetic robotic crawler vehicle of claim 12, wherein the one or more mounts are selected from the group consisting of:
   a linear bearing configured to allow one of the first and second linkages to slide linearly with respect to the chassis in one or more directions, and
   a pivot configured to allow the one of the first and second linkages to rotate about the pivot.

14. The magnetic robotic crawler vehicle of claim 13, wherein the first and second linkages are rigidly joined together such that the first and second support elements move in parallel.

15. The magnetic robotic crawler vehicle of claim 13, wherein the first and second linkages are mechanically coupled using one or more spur gears configured to synchronize the motion of the first and second support elements in one or more directions relative to the chassis and in one or more directions relative to each other.

16. The magnetic robotic crawler vehicle of claim 1, further comprising:
   one or more position sensors attached to one or more of the stabilization mechanism, the chassis and the drive wheel and configured to measure a relative position between the stabilization mechanism and either the drive wheel or the chassis; and
   a processor configured to calculate, based on a known geometry of the stabilization mechanism and the drive wheel and the relative position measured using said one or more sensors during execution of a prescribed maneuver of the robotic crawler vehicle on the surface, one or more of: a) an orientation of the robotic crawler vehicle relative to the surface based on a known geometry of the surface, and b) a curvature of the surface.

17. The robotic crawler vehicle of claim 4, further comprising:
   one or more position sensors attached to one or more of the sensor probe assembly, the chassis and the drive wheel, wherein the one or more position sensors are configured to measure a relative position between the sensor probe assembly and the drive wheel; and
   a processor configured to calculate, based on a known geometry of the sensor probe assembly and the drive wheel and the relative position measured using said one or more sensors during execution of a prescribed maneuver of the robotic crawler vehicle on the surface, one or more of: a) an orientation of the robotic crawler vehicle relative to the surface based on a known geometry of the surface, and b) a curvature of the surface.

18. A magnetic robotic crawler vehicle for traversing a surface, comprising:
   a chassis;
   a magnetic drive wheel mounted to the chassis, wherein the drive wheel extends in a lateral direction and comprises:
      two spaced apart flux concentrating yokes that rotate about a rotational axis and are configured to be driven independently thereby driving and steering the vehicle along the surface, wherein a longitudinal axis of the vehicle extends perpendicularly to the rotational axis in a front and back direction and through the midpoint between the two yokes; and
      an axially magnetized hub extending laterally between the two yokes; and
   a stabilization mechanism coupled to the chassis, the stabilization mechanism comprising:
      a first and a second support element configured to contact and move along the surface during normal operation of the vehicle, the first and second support elements being positioned on opposite sides of the drive wheel relative to the rotational axis, wherein the first and second support elements are positioned symmetrically across the rotational axis of the drive wheel and are positioned symmetrically with respect to the longitudinal axis;
      a support mechanism moveably coupling the first and second support elements to the chassis, wherein the support mechanism is configured to move the first and second support element relative to the chassis in at least an up and down direction, wherein the support mechanism is configured to move the first and second support elements in a passive manner in the up and down direction in response to a curvature of the surface thereby maintaining the support elements in contact with the surface.

19. The robotic vehicle of claim 18, the axially magnetized hub comprising:
   one or more axially magnetized magnets; and
   a housing shaped to define an open chamber therein and at least one opening through the housing that faces the surface during normal operation, wherein the chamber is provided at the midpoint between the two yokes and has a fixed position relative to the chassis,
   wherein the housing includes a left wall, a right wall and a one or more sidewalls extending therebetween, wherein the left wall and the right wall are each adjacent to a wheel component.

20. The robotic vehicle of claim 18, wherein the a housing is composed of a ferromagnetic material, and includes a left wall, a right wall and a one or more sidewalls extending therebetween, the one or more sidewalls having the at least one opening therethrough.

21. A magnetic robotic crawler vehicle for traversing a surface, comprising:
   a chassis;
   a magnetic drive wheel mounted to the chassis, wherein the drive wheel extends in a lateral direction and comprises:
      two spaced apart flux concentrating yokes that rotate about a rotational axis and which are configured to be driven independently thereby driving and steering the vehicle along the surface, wherein a longitudinal axis of the vehicle extends perpendicularly to the rotational axis in a front and back direction and through the midpoint between the two yokes,
      an axially magnetized hub extending laterally between the two yokes including,
         one or more axially magnetized magnets, and
         a housing composed of a ferromagnetic material and including a left wall, an opposing right wall and a one or more lateral walls extending therebetween along the rotational axis, the walls of the housing being shaped to define an open chamber therein and the one or more lateral walls being shaped to define at least one opening therethrough, wherein the chamber is provided at the midpoint between the two yokes and wherein the housing has a fixed position relative to the yokes such that the at least one opening faces downward toward the surface during normal operation of the vehicle; and a sensor probe assembly disposed at least partially within the chamber, the sensor probe assembly comprising:
   a dry coupled wheel probe configured to passively roll generally in a direction of travel of the vehicle along the surface, and
   a sensor support moveably coupling the wheel probe to one or more of the housing and the chassis, wherein the sensor support assembly is configured to passively move the wheel probe relative to the housing in at least an up and down direction in response to the curvature of the surface thereby maintaining the probe in contact with the surface during normal operation of the vehicle; and
a stabilization mechanism coupled to the chassis, the stabilization mechanism comprising:
   a first and a second support element configured to contact and move along the surface during normal operation of the vehicle, the first and second support elements being positioned on opposite sides of the drive wheel relative to the rotational axis, wherein the first and second support elements are positioned symmetrically across the rotational axis of the drive wheel and are positioned symmetrically with respect to the longitudinal axis, and
   a support mechanism moveably coupling the first and second support elements to the chassis, wherein the support mechanism is configured to move the first and second support element relative to the chassis in at least the up and down direction, wherein the support mechanism is passive in nature and moves the first and second support elements in at least the up and down direction in response to a curvature of the surface thereby maintaining the first and second support elements in contact with the surface.

22. The magnetic robotic crawler vehicle of claim 21, wherein the sensor support comprises one or more shafts supporting an axle of the wheel probe and being coupled to one or more of the housing and the chassis by at least one mount, wherein the at least one mount is configured to allow the one or more shafts to move relative to the housing in at least the up and down direction; and
   one or more spring elements configured exert a force between at least the sensor probe assembly and one or more of the chassis and the housing, and wherein the force urges the wheel probe downward through the at least one opening of the housing and into contact with the surface.

23. The magnetic robotic crawler vehicle of claim 21, wherein the first and second support elements are positioned equidistant from the rotational axis of the drive wheel, and one or more of: in line with the longitudinal axis of the vehicle, and evenly spaced apart from the longitudinal axis on opposite sides thereof.

24. The magnetic robotic crawler vehicle of claim 21, wherein the stabilization mechanism comprises:
   one or more linkages mechanically coupling the first and second support elements, wherein the one or more linkages are configured to move the first and second support elements symmetrically relative to the drive wheel in at least the up and down direction; and
   one or more spring elements configured exert a force between at least one of the one or more linkages and one or more of the chassis, the drive wheel and another linkage, and wherein the force urges the front and rear support elements into contact with the surface thereby urging the first chassis sections into a normal position relative to the surface.

* * * * *